United States Patent [19]

Westall et al.

[11] 3,984,394

[45] Oct. 5, 1976

[54] SALTS OF DIHYDROCHALCONE DERIVATIVES AND THEIR USE AS SWEETENERS

[75] Inventors: Edward B. Westall, San Jacinto; Alan W. Messing, Hemet, both of Calif.

[73] Assignee: Nutrilite Products, Inc., Buena Park, Calif.

[22] Filed: May 14, 1971

[21] Appl. No.: 143,632

[52] U.S. Cl.................................. 536/8; 426/548
[51] Int. Cl.$^2$.................................. C07H 15/04
[58] Field of Search.............................. 260/210 F

[56] References Cited
UNITED STATES PATENTS

| | | | |
|---|---|---|---|
| 2,926,162 | 2/1960 | Hart | 260/210 F |
| 3,086,970 | 4/1963 | Sakieki et al. | 260/210 F |
| 3,087,821 | 4/1963 | Horowitz et al. | 260/210 F |
| 3,375,242 | 3/1968 | Horowitz et al. | 260/210 F |
| 3,422,086 | 1/1969 | Carron et al. | 260/210 F |
| 3,429,873 | 2/1969 | Horowitz et al. | 260/210 F |
| 3,522,236 | 7/1970 | Kreechek et al. | 260/210 F |

*Primary Examiner*—Johnnie R. Brown
*Attorney, Agent, or Firm*—Burns, Doane, Swecker & Mathis

[57] ABSTRACT

New compounds which are monobasic metal salts of dihydrochalcones and the method of their preparation, the monosodium, monopotassium, and monocalcium salts being useful as sugar substitutes and sweetening agents for foods and beverages.

4 Claims, No Drawings

SALTS OF DIHYDROCHALCONE DERIVATIVES AND THEIR USE AS SWEETENERS

BACKGROUND OF THE INVENTION

This invention relates to sweetening agents which may be employed as sugar substitutes in a wide variety of food, beverage, and confectionary products.

Various dihydrochalcones and their organic derivatives have been proposed in the prior art as sugar substitutes and sweeteners. In U.S. Pat. No. 3,087,821 there are disclosed various compounds having a high degree of individual sweetness, such as neohesperidin dihydrochalcone, naringin dihydrochalcone, and prunin dihydrochalcone. These compounds are prepared by known methods from the corresponding flavanone glycosides, such as neohesperidin, naringin, prunin and the like, which occur naturally in citrus and other fruits, and which may be recovered as a by-product of the fruit processing operations.

In the preparation of the respective dihydrochalcones, the flavanone glycosides are dissolved in strong caustic alkalies, such as sodium or potassium hydroxide solutions, such solutions having concentrations of the order of 10% to 25% by weight. The action of the alkali is to convert the flavanone glycoside to the corresponding chalcone. The alkali-solubilized flavanone glycoside is then transferred rapidly to an acid environment and subjected to strong acid hydrolysis to avoid separation of the flavanone glycoside, and to permit formation of the chalcone. Then the chalcone is catalytically reduced with hydrogen to form the dihydrochalcone derivative.

Various processes for the preparation of dihydrochalcone derivatives which follow the foregoing basic principles are additionally described in U.S. Pat. Nos. 2,700,047; 3,375,242; 3,364,196; 3,429,873; and 3,522,236. U.S. Pat. NO. 3,429,873 discloses the preparation of hesperitin dihydrochalcone glucoside, a compound of intense sweetness, from the starting material hesperidin which is itself tasteless. U.S. Pat. No. 3,522,236 describes a propoxy ether of a neohesperidin type dihydrochalcone which also possesses a high level of sweetness.

In all the processes described in the foregoing patents, there is formed, as a result of the initial alkali treatment, a water soluble alkali salt of the corresponding chalcone, by reaction of the phenolic hydroxyl groups in the flavanone nucleus. When this alkali salt is acidified, the free chalcone is obtained, which is then hydrogenated to the dihydrochalcone. Thus, at no time is there any formation of an alkali salt of the dihydrochalcone product. Moreover, the high concentration of alkali employed, ranging from 10% to 25%, which corresponds to 3 or 4 moles of alkali per mole of flavanone, insures that all of the available hydroxyl groups present are neutralized. The art has recognized, moreover, that the use of less than this molar ratio, for example, 2 moles of alkali, was insufficient to form the desired chalcone. The maintenance of a sufficiently high molar ratio of alkali to flavanone to effect chalconization is described in U.S. Pat. No. 2,700,047, which indicates that to completely chalconize hesperidin, the requisite ratio of alkali to hesperidin would be about 3 moles alkali to 1 mole hesperidin. However, as pointed out above, no alkali treatment of the final dihydrochalcone compounds themselves is disclosed or contemplated, nor any salts of those dihydrochalcones which were known to be sweet when in their nonionic forms.

GENERAL DESCRIPTION OF THE INVENTION

In accordance with the present invention there are provided novel monobasic metal salts of dihydrochalcone having the following formula:

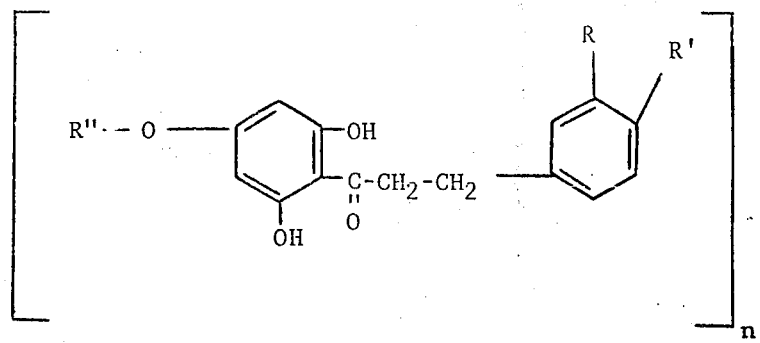

wherein R is selected from the group consisting of hydrogen and hydroxy, R' is selected from the group consisting of hydroxy, methoxy, ethoxy and propoxy, and R" is selected from the group consisting of neohesperidosyl, $\beta$-rutinosyl and $\beta$-D-glucosyl, M is a mono- or divalent metal selected from the group consisting of an alkali metal and an alkaline earth metal, and n is an integer from 1 to 2 corresponding to the valence of the selected metal M.

Typical compounds of the above formula are the alkali or alkaline earth metal monosalts of the following:

Neokesperidin dihydrochalcone, having the formula:

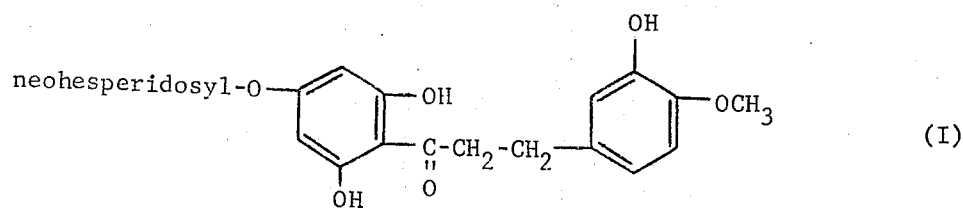

(I)

2', 4', 6', 3-tetrahydroxy-4-n-propoxydihydrochalcone 4'-βneohesperidoside having the formula:

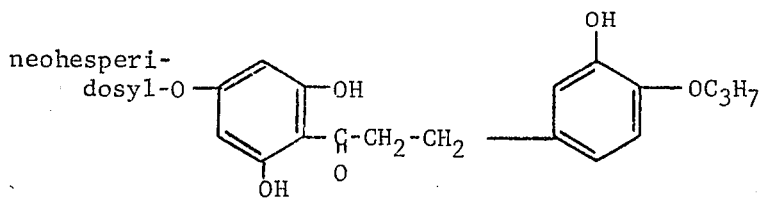

(II)

naringin dihydrochalcone of the formula:

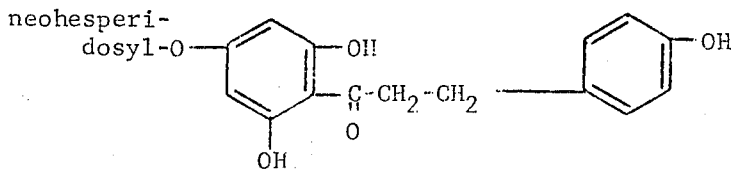

(III)

prunin dihydrochalcone of the formula:

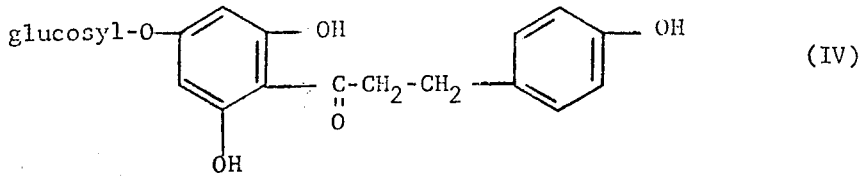

(IV)

hesperidin dihydrochalcone having the formula:

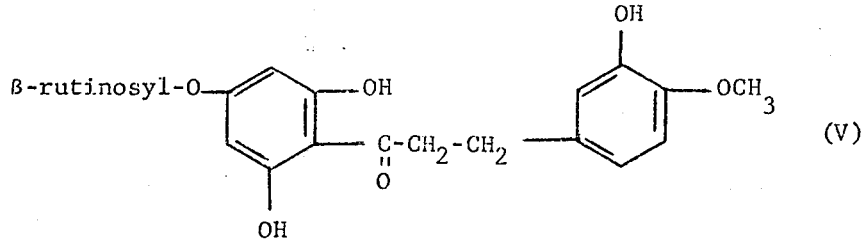

(V)

and hesperitin dihydrochalcone glucoside having the formula:

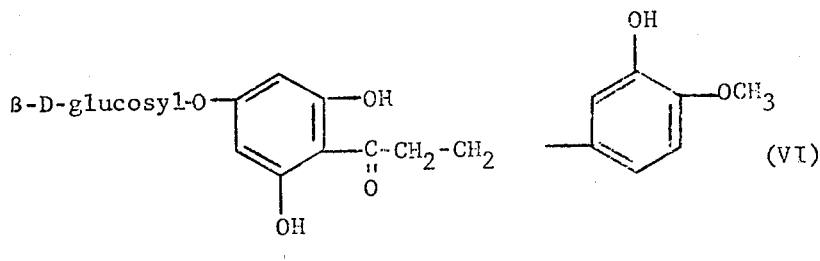

(VI)

In the foregoing general formula the term alkali metal includes sodium, potassium, lithium, rubidium, caesium, and ammonium, while the term alkaline earth metal includes calcium, strontium and barium.

The general method of preparation of the novel monobasic metal salts of dihydrochalcones, in accordance with the invention, involves the reaction of an alkali metal or alkaline earth metal hydroxide, oxide, or salt with a mole equivalent of the dihydrochalcone in an aqueous medium, i.e., in a molar ratio of 1 mole of alkali metal compound to 1 mole of the dihydrochalcone, or in the case of an alkaline earth metal compound, 0.5 mole of alkaline earth metal compound to 1 mole of the dihydrochalcone compound. In the case of alkali metal reactants the hydroxide is preferably employed owing to its ready solubility in the aqueous medium. However, in the case of the more limited solubility of alkaline earth compounds, the hydroxide, while preferable, may be introduced in the form of an aqueous suspension. In both cases the dihydrochalcone compound reacts with the base to form a clear aqueous solution. In the reaction product, in each case, only one of the three free phenolic hydroxyl groups originally present in the dihydrochalcone compound undergoes salt formation. Where an alkali metal salt is formed the resulting compound will be a monosodium, monopotassium, and the like, salt. Where the alkaline earth metal is involved, 2 moles of the dihydrochalcone compound react with the metal, with only 1 of the phenolic hydroxyls in each mole undergoing salt formation.

According to their respective properties, the foregoing salts may find use in a variety of applications. Thus the lithium compound may be used industrially or for specifically medicinal applications. The barium compounds may be used, for example, as X-ray contrast media. These represent applications in which taste is of little or no importance.

In accordance with an important aspect of the present invention, it has been found that certain of the monobasic metal salts of the various dihydrochalcones unexpectedly exhibit improved properties of sweetness in comparison with the corresponding dihydrochalcones which are known to be sweet per se in their nonionic forms. The monobasic salt derivatives of the invention are characterized in general by a higher degree of solubility and a shorter duration of sweetness than the parent dihydrochalcone compounds. Many of the latter are much lower in solubility than the novel salt derivative sweetners of the invention and possess a persistence of taste which the salt derivatives do not and which in certain applications is undesirable. This opens up new fields of use to those monobasic salts derived from non-toxic metals such as sodium, potassium, ammonium, and calcium, permitting their use as a substitute for sugars in the diets of patients having diabetic or other abnormal metabolic symptons. The monobasic salts of the invention also, in view of their high level of sweetness and short taste persistence characteristics, may be used in beverages, soft drinks, confectionery, desserts and the like, particularly for dietetic purposes when non-persistence and a minimum after taste, coupled with a high degree of sweetness are sought after qualities. In the case of persons who are restricted to a low sodium diet, the potassium or calcium derivatives may be applied.

The sweetening agents of the invention offer a considerably higher degree of solubility as salts than do the parent compounds from which they are derived and possess greater stability both in dry form and in solution than do the parent materials. The salts possess a considerably different taste and duration of taste sensation than the corresponding parent compounds.

DESCRIPTION OF THE PREFERRED EMBODIMENTS

The following examples serve to illustrate the practice of the invention, but are not to be regarded as limiting:

EXAMPLE 1

Sodium Salt of Neohesperidin Dihydrochalcone 0.65 gms. of NaOH (0.0163 moles) are dissolved at room temperature in 25 ml. $H_2O$ with stirring. 10 gms. of neohesperidin dihydrochalcone (0.0163 moles) is added, which all dissolves. Additional neohesperidin dihydrochalcone is added until no more would dissolve. The solution is filtered and the water removed under vacuum. The resulting solid is yellowish red in color after grinding. The material dissolves readily in water, being soluble therein in concentration greater than 1 gm/ml., is very many times sweeter than sucrose, and exhibits markedly different taste aspects than the parent material. Decomp. Pt. 172° – 173°C. The analysis is:

|   | Theo. | Actual |   |
|---|-------|--------|---|
| C | 52.99 | 53.14  | Moisture = 6.26 |
| H | 5.56  | 5.54   |   |
| Na| 3.63  | 3.86   |   |

EXAMPLE 2

Calcium Salt of Neohesperidin Dihydrochalcone 0.605 gms of $Ca(OH)_2$ (0.0081 mole) is suspended, with stirring, in 50 ml of distilled $H_2O$. The slurry is milky in appearance. 10 gms. of neohesperidin dihydrochalcone (0.0163 moles) is added over a period of 10 minutes as a solid. After the first few portions the $Ca(OH)_2$ dissolves and the solution becomes clear and yellow. After 10 gms. is added 3 additional portions are added until no more neohesperidin dihydrochalcone dissolves. The deep green solution is filtered, removing excess neohesperidin dihydrochalcone and the material is freeze dried.

The product dissolves readily in water having a solubility greater than 1 gm/ml. and has markedly different taste aspects than the parent material.

What is claimed is:

1. As a dietetic sweetner, a monobasic metal salt of a dihydrochalcone of the formula:

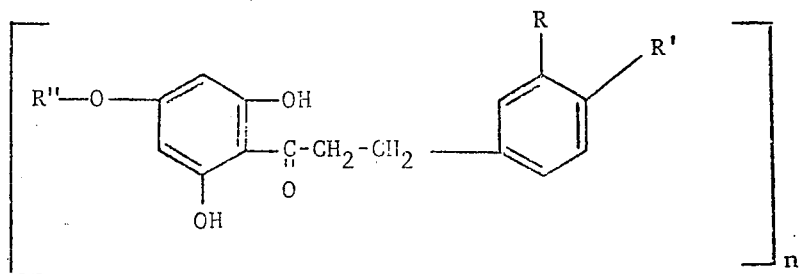

wherein R is selected from the group consisting of hydrogen and hydroxy, R' is selected from the group consisting of hydroxy and $C_1$ to $C_3$ alkoxy, and R'' is selected from the group consisting of neohesperidosyl, β-rutinosyl, and β-D-glucosyl, M is a mono- or divalent non-toxic metal selected from the group consisting of alkali metals and alkaline earth metals, and n is an integer corresponding to the valence of said selected metal M.

2. As a dietetic sweetner, the monosodium salt of neohesperidin dihydrochalcone.

3. As a dietetic sweetner, the monocalcium salt of neohesperidin dihydrochalcone.

4. As a dietetic sweetener, a monobasic metal salt of a dihydrochalcone of the formula:

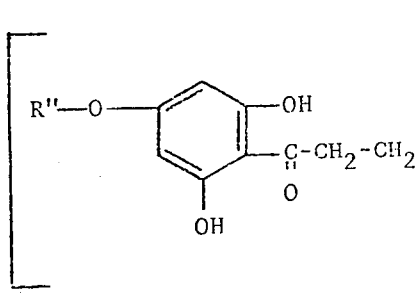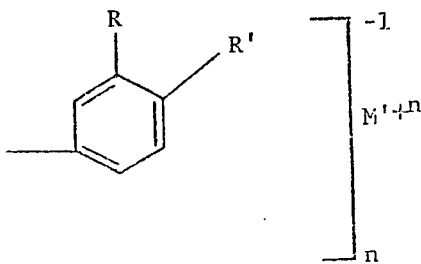
wherein R is selected from the group consisting of hydrogen and hydroxy, R' is selected from the group consisting of hydroxy and methoxy, and R'' is selected from the group consisting of neohesperidosyl, β-rutinosyl and β-D-glucosyl, n is an integer from 1 to 2, and M' is selected from the group consisting of sodium, potassium, ammonium and calcium.
* * * * *